United States Patent
Hete

(10) Patent No.: US 10,758,157 B2
(45) Date of Patent: Sep. 1, 2020

(54) DETERMINING IF AIRWAY CLEARANCE IS REQUIRED DURING RESPIRATORY THERAPY

(71) Applicant: KONINKLIJKE PHILIPS N.V., Eindhoven (NL)

(72) Inventor: Bernard F. Hete, Kittanning, PA (US)

(73) Assignee: Koninklijke Philips N.V., Eindhoven (NL)

( * ) Notice: Subject to any disclaimer, the term of this patent is extended or adjusted under 35 U.S.C. 154(b) by 605 days.

(21) Appl. No.: 15/520,430

(22) PCT Filed: Oct. 13, 2015

(86) PCT No.: PCT/IB2015/057813
§ 371 (c)(1),
(2) Date: Apr. 20, 2017

(87) PCT Pub. No.: WO2016/063172
PCT Pub. Date: Apr. 28, 2016

(65) Prior Publication Data
US 2017/0303821 A1    Oct. 26, 2017

Related U.S. Application Data

(60) Provisional application No. 62/068,279, filed on Oct. 24, 2014.

(51) Int. Cl.
*A61B 5/00* (2006.01)
*A61B 5/091* (2006.01)
(Continued)

(52) U.S. Cl.
CPC .............. *A61B 5/091* (2013.01); *A61B 5/087* (2013.01); *A61B 5/4836* (2013.01);
(Continued)

(58) Field of Classification Search
CPC .......... A61M 2016/0027; A61M 16/16; A61M 2016/0039; A61M 16/06; A61M 16/0666;
(Continued)

(56) References Cited

U.S. PATENT DOCUMENTS 5,803,066 A * 9/1998 Rapoport ............. A61B 5/0002
128/204.21
5,970,975 A * 10/1999 Estes ................... A61M 16/024
128/204.18

(Continued)

FOREIGN PATENT DOCUMENTS

WO    WO03045250 A2    6/2003

OTHER PUBLICATIONS

Dhand R., "Ventilator Graphics and Respiratory Mechanics in the Patient With Obstructive Lung Disease", Respiratory Care, Feb. 2005 (Feb. 2005), pp. 246-260, XP055261849, Retrieved from the Internet: URL:http://servi ces.aarc.org/source/DownloadDocument/Downloaddocs/02.05.0246.pdf [retrieved on Mar. 31, 2016].

(Continued)

*Primary Examiner* — May A Abouelela
(74) *Attorney, Agent, or Firm* — Daniel H. Brean

(57) ABSTRACT

This disclosure relates to a system configured to detect the presence of secretions in a subject's airway during respiratory therapy. The system can determine whether the subject requires airway clearance. A pressure generator generates a pressurized flow of breathable gas. Sensors generate output signals relating to one or more gas parameters of the pressurized flow of breathable gas. The system can determine a first parameter that is an indication of the volume of breathable gas within the airway of the subject and a time derivative of the first gas parameter to generate a plot of these parameters. The plot includes a perimeter and an area that can be used to determine whether to effectuate initiation (Continued)

of airway clearance based on a complete breathing cycle that includes at least one inhalation and exhalation.

8 Claims, 3 Drawing Sheets

(51) Int. Cl.
*A61B 5/087* (2006.01)
*A61M 16/00* (2006.01)

(52) U.S. Cl.
CPC .... *A61M 16/0006* (2014.02); *A61M 16/0051* (2013.01); *A61M 16/026* (2017.08); *A61M 16/0063* (2014.02); *A61M 2016/003* (2013.01); *A61M 2016/0027* (2013.01); *A61M 2205/332* (2013.01); *A61M 2205/3306* (2013.01); *A61M 2205/502* (2013.01); *A61M 2205/52* (2013.01); *A61M 2230/06* (2013.01); *A61M 2230/42* (2013.01); *A61M 2230/63* (2013.01)

(58) Field of Classification Search
CPC .......... A61M 16/0057; A61M 16/0066; A61M 16/00; A61M 16/107; A61M 2202/0208; A61M 2205/3334; A61M 2205/50; A61M 2205/3331; A61K 9/0043; A61K 9/0078; A61B 5/0816; A61B 2562/0247; A61B 5/4836; A61B 17/12104; A61B 1/267; A61B 2017/248
USPC ............... 600/529, 538; 702/19; 128/204.18, 128/204.23, 203.23
See application file for complete search history.

(56) References Cited

U.S. PATENT DOCUMENTS

| | | | |
|---|---|---|---|
| 5,984,872 A | 11/1999 | Vriend | |
| 6,183,423 B1* | 2/2001 | Gaumond | A61B 5/085 600/529 |
| 6,287,264 B1* | 9/2001 | Hoffman | A61B 5/0809 600/529 |
| 6,467,477 B1* | 10/2002 | Frank | A61M 16/024 128/203.23 |
| 8,357,100 B2* | 1/2013 | Eriksen | A61B 5/087 600/538 |
| 8,424,529 B2* | 4/2013 | Efrati | A61M 16/044 128/207.14 |
| 8,638,200 B2* | 1/2014 | Milne | A61B 5/0803 340/286.07 |
| 2003/0100843 A1* | 5/2003 | Hoffman | A61B 5/0809 600/538 |
| 2005/0251056 A1* | 11/2005 | Gribkov | A61B 5/0452 600/509 |
| 2006/0070624 A1* | 4/2006 | Kane | A61M 16/0003 128/204.23 |
| 2008/0202528 A1* | 8/2008 | Carter | A61M 16/0051 128/204.23 |
| 2011/0270116 A1* | 11/2011 | Freitag | A61B 5/6852 600/538 |
| 2012/0003620 A1* | 1/2012 | Pittman | A61M 16/00 434/262 |
| 2012/0138057 A1* | 6/2012 | Tham | A61M 16/024 128/204.23 |
| 2012/0226444 A1* | 9/2012 | Milne | A61B 5/08 702/19 |
| 2014/0000610 A1* | 1/2014 | Rapoport | A61M 16/0066 128/204.23 |
| 2014/0032120 A1 | 1/2014 | Eriksen | |
| 2014/0066749 A1* | 3/2014 | Dickerson | A61B 5/7285 600/413 |
| 2015/0230750 A1* | 8/2015 | McDarby | A61B 5/0816 600/407 |
| 2016/0015918 A1* | 1/2016 | Kuriger | A61M 16/0051 128/204.23 |
| 2016/0135713 A1* | 5/2016 | Chbat | A61M 16/00 600/538 |
| 2017/0303821 A1* | 10/2017 | Hete | A61M 16/0051 |

OTHER PUBLICATIONS

Zhiwei Huang et al., "Realization of a Monitoring System of Respiratory Mechanics Parameters based on Sensors", Bioelectronics and Bioinformatics (ISBB), 2011 International Symposium on, IEEE, Nov. 3, 2011 (Nov. 3, 2011), pp. 206-209, XP032076741.

Jubran A. et al., "Use of Flow-Volume Curves in Detecting Secretions in Ventilator-Dependent patients", American Journal of Respiratory and Critical Care Medicine, vol. 1, 150, No. 3, Sep. 1994 (Sep. 1994), pp. 766-769, XP008179646.

Zapletal A. et al., "Area under the Maximum Expiratory Flow-Volume Curve—A Sensitive Parameter in the Evaluation of Airway Patency", Respiration 2008;75:40-47 http://www.karger.com/Article/Pdf/99615.

* cited by examiner $$\Phi = \frac{P^2}{A}$$

| Common Shape | Φ |
|---|---|
| Square | 16 |
| Rectangle (height h, base nh) | n = 2 → 18<br>n = 3 → 21.3 |
| Circle | 12.6 |
| Equilateral Triangle | 20.8 |
| Isosceles Triangle (base h, side nh) | n = 1.5 → 24.6<br>n = 2 → 28.9 |
| Ellipse (minor axis β, major axis nβ) | n = 2 → 15.7<br>n = 3 → 20.9 |

DETERMINING IF AIRWAY CLEARANCE IS REQUIRED DURING RESPIRATORY THERAPY

CROSS-REFERENCE TO RELATED APPLICATIONS

This patent application claims the priority benefit under 35 U.S.C. § 371 of international patent application no. PCT/IB215/057813, filed Oct. 12, 2015, which claims the priority benefit under 35 U.S.C. § 119(e) of U.S. Provisional Application No. 62/068,279 filed on Oct. 24, 2014, the contents of which are herein incorporated by reference.

BACKGROUND OF THE INVENTION

1. Field of the Invention

The present disclosure pertains to a method and apparatus for monitoring the airway of a subject during respiratory therapy to determine if the subject requires airway clearance.

2. Description of the Related Art

It is well known that secretions can develop in the airway of a subject receiving respiratory therapy. Often when a subject is intubated, the physical presence of foreign material and/or pressure on the oral and lung tissue of the subject may generate secretions in the airway of the subject. In some circumstances, respiratory therapy must be discontinued until the secretions can be cleared from the airway of the subject.

SUMMARY OF THE INVENTION

Accordingly, one or more aspects of the present disclosure relate to a system configured to detect presence of secretions in an airway of a subject during respiratory therapy and determine whether the subject requires airway clearance. The system includes a pressure generator configured to generate a pressurized flow of breathable gas for delivery to the airway of the subject; one or more sensors configured to generate output signals that convey information related to one or more gas parameters of the pressurized flow of breathable gas delivered to the airway of the subject; one or more physical computer processors operatively connected to the pressure generator and the one or more sensors. The one or more physical computer processors configured by computer readable instructions to: determine a first gas parameter that indicates a volume of breathable gas within the airway of the subject and a second gas parameter that is a time derivative of the first gas parameter; and determine whether to effectuate initiation of airway clearance for the subject based on a perimeter of a plot of the first gas parameter versus the second gas parameter for a complete breathing cycle that includes an inhalation and an exhalation.

Yet another aspect of the present disclosure relates to a method configured to detect a presence of secretions in an airway of a subject during respiratory therapy and determine whether the subject requires airway clearance. The method includes generating a pressurized flow of breathable gas for delivery to the airway of the subject; generating output signals that convey information related to one or more gas parameters of the pressurized flow of breathable gas delivered to the airway of the subject; determining a first gas parameter that indicates volume of breathable gas within the airway of the subject and a second gas parameter that is a time derivative of the first gas parameter; and determining whether to effectuate initiation of airway clearance for the subject based on a perimeter of a plot of the first gas parameter versus the second gas parameter for a complete breathing cycle that includes an inhalation and an exhalation.

Still another aspect of present disclosure relates to a system configured to detect a presence of secretions in an airway of a subject during respiratory therapy and determine whether the subject requires airway clearance. The system includes means for generating a pressurized flow of breathable gas for delivery to the airway of the subject; means for generating output signals that convey information related to one or more gas parameters of the pressurized flow of breathable gas delivered to the airway of the subject; means for determining a first gas parameter that indicates volume of breathable gas within the airway of the subject and a second gas parameter that is a time derivative of the first gas parameter; and means for determining whether to effectuate initiation of airway clearance for the subject based on a perimeter of a plot of the first gas parameter versus the second gas parameter for a complete breathing cycle that includes an inhalation and an exhalation.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
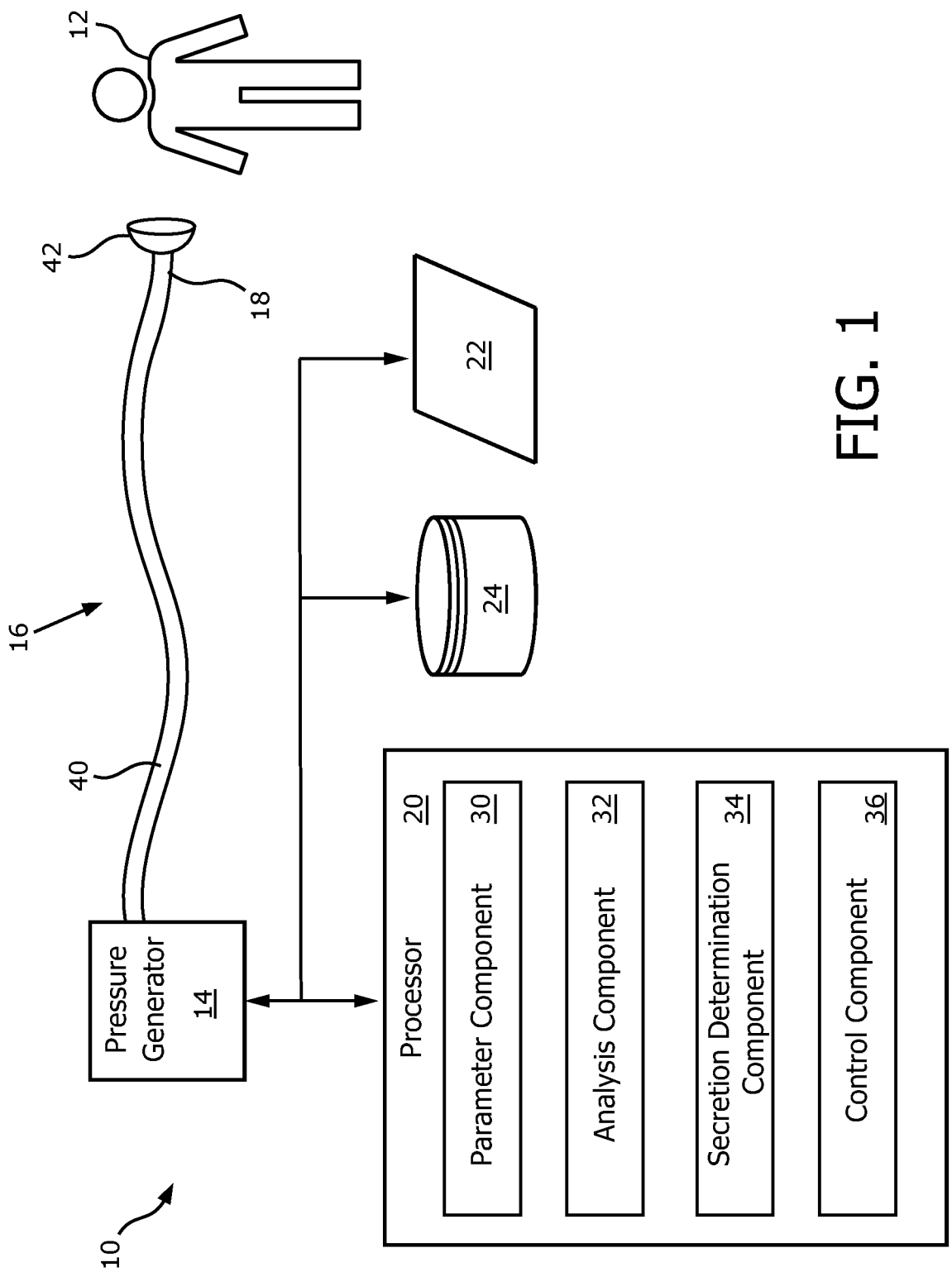
FIG. 1 is an illustration of one embodiment of a secretion detection system configured to determine whether a subject requires airway clearance.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to detect presence of secretions in an airway of a subject 12 during respiratory therapy and determine whether the subject requires airway clearance. In some embodiments, system 10 includes one or more of a pressure generator 14, a subject interface 16, a sensor 18, a physical computer processor 20, a user interface 22, electronic storage 24, and/or other components.

During respiratory therapy airways may become clogged by tissue secretions which can result in decreased gas delivery to a subject 12. Clearing the airways is sometimes necessary to continue respiratory therapy. System 10 determines when clearance is required. System 10 plots parameters associated with the respiratory therapy (e.g., a flow rate and a volume of breathable gas) during the inhalations and exhalations of subject 12. System 10 is configured to analyze a perimeter of the plot and an area of the plot to determine presence of secretions that require airway clearance. In one embodiment, the analysis includes a square of the perimeter of a geometric shape of the plot normalized by the area of the geometric shape of the plot to determine a dimensionless number that can be used to determine when the airway requires clearance.

Pressure generator 14 is configured to generate a pressurized flow of gas for delivery to the airway of subject 12. Pressure generator 14 may control one or more parameters of the flow of gas (e.g., flow rate, pressure, volume, temperature, gas composition, timing, etc.) for therapeutic purposes, and/or for other purposes. By way of a non-limiting example, pressure generator 14 may be configured to control a pressure level of the flow of gas during inhalation and/or exhalation of subject 12 to provide pressure support, inexsufflation therapy, ventilation therapy, and/or other therapies to the airway of subject 12.

Pressure generator 14 receives a flow of gas from a gas source, such as the ambient atmosphere, and elevates the pressure of that gas for delivery to the airway of subject 12. In some embodiments, pressure generator 14 receives a flow of gas from a gas source. Pressure generator 14 is any device, such as, for example, a pump, blower, piston, compressor, pressurized wall gas, bellows, and/or other device that is capable of elevating the pressure of the received gas for delivery to subject 12. Pressure generator 14 may comprise one or more valves for controlling the pressure/flow of gas. The present disclosure also contemplates controlling the operating speed of the blower, either alone or in combination with such valves, to control the pressure/flow of gas provided to the patient.

Subject interface 16 is configured to communicate the pressurized flow of breathable gas to the airway of subject 12. As such, subject interface 16 comprises conduit 40, interface appliance 42, and/or other components. Conduit 40 is configured to convey the pressurized flow of gas to interface appliance 42. Conduit 40 may be and/or include a length of tubing and/or other components configured to convey the pressurized flow of gas to interface appliance 42. Interface appliance 42 is configured to deliver the flow of gas to the airway of subject 12. In some embodiments, interface appliance 42 is configured to be non-invasively engaged by the mouth and/or other orifices of subject 12. Non-invasive engagement comprises removably engaging one or more external orifices of the airway of subject 12 (e.g., nostrils and/or mouth) to communicate gas between the airway of subject 12 and interface appliance 42.

In some embodiments, interface appliance 42 is removably coupled to conduit 40. Interface appliance 42 may be removed for cleaning and/or for other purposes. In some embodiments, one end of conduit 40 is configured as a mouthpiece to be engaged by the mouth of subject 12.

In some embodiments, other non-invasive interface appliances may be configured as interface appliance 42. Some examples of non-invasive interface appliance 42 may comprise, for example, a nasal cannula, a nasal mask, a nasal/oral mask, a full face mask, a total face mask, tracheostomy tube, endotracheal tube, and/or other interface appliances that communicate a flow of gas with an airway of a subject. The present disclosure is not limited to these examples, and contemplates delivery of the flow of gas to the subject using any interface appliance. In some embodiments, system 10 may be connected to a classical respiratory circuit (e.g., a six foot hose) such that the classical respiratory circuit functions as subject interface 16.

Sensor 18 is configured to generate output signals that convey information related to one or more gas parameters of the breathable gas delivered to the airway of subject 12. Sensor 18 may comprise one or more sensors that generate such information directly. For example, sensor 18 may include pitot tubes configured to detect pressures of breathable gas along subject interface 16 resulting from inhalation and/or exhalations of subject 12. For example, sensor 18 may detect the pressure, flow, flow rate, volume, and/or other parameters pertaining to the inhalation and/or exhalations of subject 12. Sensor 18 may comprise one or more sensors that generate output signals conveying information related to inhalations and/or exhalations of subject 12 indirectly. For example, one or more sensors 18 may generate an output based on a heart rate of subject 12 (e.g., sensor 18 may be a heart rate sensor located on the chest of subject 12, and/or be configured as an optical sensor included in a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), changes in skin color of subject 12 (e.g., sensor 18 may include a camera that can detect changes is skin color of subject 12 and infer vital signs such as heart rate, breathing rate, and/or other vital signs from the changes in color), respiration of subject 12, and/or other characteristics of subject 12. Although sensor 18 is illustrated at a single location in fluid communication with subject interface 16, this is not intended to be limiting. Sensor 18 may include sensors disposed in a plurality of locations, such as for example, within (or in communication with) conduit 40, interface appliance 42, pressure generator 14, on subject 12, and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., subject interface 16, user interface 22), and/or processor 20 may represent processing functionality of a plurality of devices operating in coordination.

As shown in FIG. 1, processor 20 is configured to execute one or more computer program components. The one or more computer program components may comprise one or more of a parameter component 30, an analysis component 32, a secretion determination component 34, a control component 36, and/or other components. Processor 20 may be configured to execute components 30, 32, 34, and/or 36 by software; hardware; firmware; some combination of software, hardware, and/or firmware; and/or other mechanisms for configuring processing capabilities on processor 20.

It should be appreciated that although components 30, 32, 34, and 36 are illustrated in FIG. 1 as being co-located within a single processing unit, in embodiments in which processor 20 comprises multiple processing units, one or more of components 30, 32, 34, and/or 36 may be located remotely from the other components. The description of the functionality provided by the different components 30, 32, 34, and/or 36 described below is for illustrative purposes, and is not intended to be limiting, as any of components 30, 32, 34, and/or 36 may provide more or less functionality than is described. For example, one or more of components 30, 32, 34, and/or 36 may be eliminated, and some or all of its functionality may be provided by other components 30, 32, 34, and/or 36. As another example, processor 20 may be configured to execute one or more additional components that may perform some or all of the functionality attributed below to one of components 30, 32, 34, and/or 36.

Parameter component 30 is configured to determine one or more parameters of the pressurized flow of breathable gas. The one or more parameters may comprise gas parameters related to the pressurized flow of breathable gas, breathing parameters related to the respiration of subject 12, and/or other parameters. Parameter component 30 is configured to determine the one or more parameters based on the output signals of sensors 18, and/or other information. The information determined by parameter component 30 may be used for controlling pressure generator 14, stored in electronic storage 24, generating a plot (described below), and/or used for other uses.

The one or more parameters determined by parameter component 30 may include, for example, one or more of a flow rate, a volume, a pressure, humidity, a temperature, an acceleration, a velocity, a timing (e.g., beginning and/or end of inhalation, beginning and/or end of exhalation, etc.), a respiration rate, a duration (e.g., of inhalation, of exhalation, of a single breathing cycle, etc.), respiration frequency, peak flows, peak pressures, and/or other parameters. For example, parameter component 30 may be configured to determine a first gas parameter that indicates a volume of breathable gas within the airway of subject 12 and a second gas parameter that is a time derivative of the first gas parameter (e.g., flow rate). In some embodiments, the parameters may be determined at one or more individual points in time during respiratory therapy. In some embodiments, the parameters may be determined at one or more sampling rates. The one or more sampling rates may be determined at manufacture, determined based on previous respiration of subject 12, determined based on information entered and/or selected via user interface 22, determined by one or more of the other components of processor 20, and/or determined in other ways.

Parameter component 30 is configured to plot one or more of the determined parameters on a two-dimensional plot. Individual points on a given plot correspond to values of parameters at individual points in time. In some embodiments, parameter component 30 is configured such that the volume of gas within the airway of subject 12 is plotted through time along one axis of a two dimensional graph. Similarly, parameter component 30 may determine a time derivative of the volume of gas within the airway of subject 12 and plot this parameter for individual points in time (e.g., flow rate) through time on an orthogonal axis of the two dimensional graph. In some embodiments, the time derivative of the volume of gas for individual points in time is and/or or is determined based on the flow rate of gas delivered to subject 12. In some embodiments, plotted points may be a sampling of values of one or more parameters determined at individual points in time.

Figure 2:
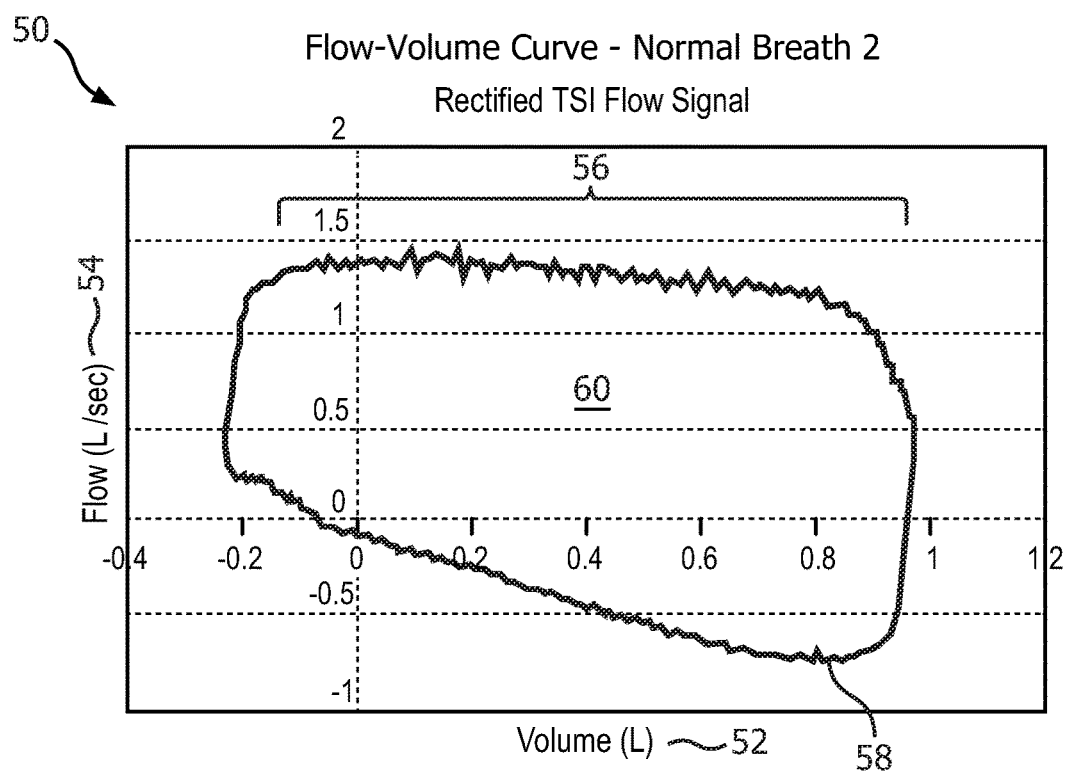
FIG. 2 is a plot of flow rate versus volume during at least one inspiration and expiration of a subject.

FIG. 2 illustrates a plot 50 of the volume of gas 52 within the airway of subject 12 versus the flow rate of gas 54 delivered to subject 12. FIG. 2 illustrates the inhalation and exhalation of subject 12 in an unobstructed airway. FIG. 2 shows a normal healthy inspiration and expiration volume for subject 12. The plot in FIG. 2 forms a geometric shape (e.g., a generally oval and/or elliptical shape) that has a perimeter 58 and an area 60. The plot shown in FIG. 2 lacks significant noise 56 in perimeter 58 and is relatively smooth. In some embodiments, the plot 50 may generate a flow volume loop, a pressure volume loop, a pressure flow loop, and/or other geometric shapes that indicate parameters of inhalation and exhalation of subject 12.

Referring to FIG. 1 and FIG. 2, in some embodiments, analysis component 32 is configured to determine the perimeter 58 and/or the area 60 of plot 50 shown in FIG. 2. Analysis component 32 is configured to normalize perimeter 58 by a factor corresponding to the area 60 of plot 50. In some embodiments, analysis component 32 is configured to normalize perimeter 58 by area 60. In some embodiments, analysis component 32 is configured to raise perimeter 58 to an exponential power to enhance a noise signal in perimeter 58. Analysis component 32 enhances the noise signal because the noise signal is indicative of the need for airway clearance in subject 12. By way of a non-limiting example, analysis component 32 may be configured to determine perimeter 58 of plot 50, determine area 60 of plot 50, square perimeter 58, and normalize perimeter 58 by area 60 to produce a dimensionless metric. In some embodiments, the dimensionless metric produced by the perimeter squared divided by an area is indicative of whether the subject requires airway clearance. For example, a dimensionless metric for a clear breathing cycle (e.g., no secretions present) can be determined and then compared to a dimensionless metric for a current breathing cycle (this comparison is described below). In some embodiments, the dimensionless metric is defined by the parameter Φ as provided by the following equation:

$$\Phi = \frac{P^2}{A}$$

where P is the perimeter 58 and A is the area 60 of the plot 50 generated by parameter component 30. Dimensionless number Φ has the same value regardless of the size of the geometric shape formed in plot 50. This makes Φ a value that may be relatively constant for a subject's individual inspiration and expiration pattern (e.g., when secretions are not present), regardless of the size, lung capacity, and/or other characteristics of subject 12. Dimensionless number Φ for a current breathing cycle can thus be compared to a secretion free baseline and/or threshold breathing cycle. The comparison of dimensionless metrics for the current breathing cycle and the baseline and/or threshold breathing cycle provides an indication of whether secretions requiring clearance are present, regardless of the characteristics (e.g., size, lung capacity, etc.) of subject 12.

Returning to FIG. 1, secretion determination component 34 is configured to determine whether to effectuate initiation of airway clearance for subject 12. Secretion determination component 34 is configured to determine whether to effectuate initiation of airway clearance based on the determined perimeter and/or area of a plot (e.g., perimeter 58 and area 60 of plot 50 shown in FIG. 2) of the first gas parameter versus the second gas parameter for a complete breathing cycle that includes an inhalation and an exhalation, based on values of Φ for a current breathing cycle and/or one or more baseline and/or threshold breathing cycles, and/or other information. In some embodiments secretion determination component 34 may compare the dimensionless number Φ determined by analysis component 32 to a threshold value (e.g., baseline value) for Φ to determine if the airway of subject 12 requires clearance. For example, secretion determination component 34 may determine a threshold value for Φ based on previous respiration of subject 12 and compare the threshold value to a current value of Φ determined by analysis component 32 for a current breathing cycle of subject 12.

Figure 3:
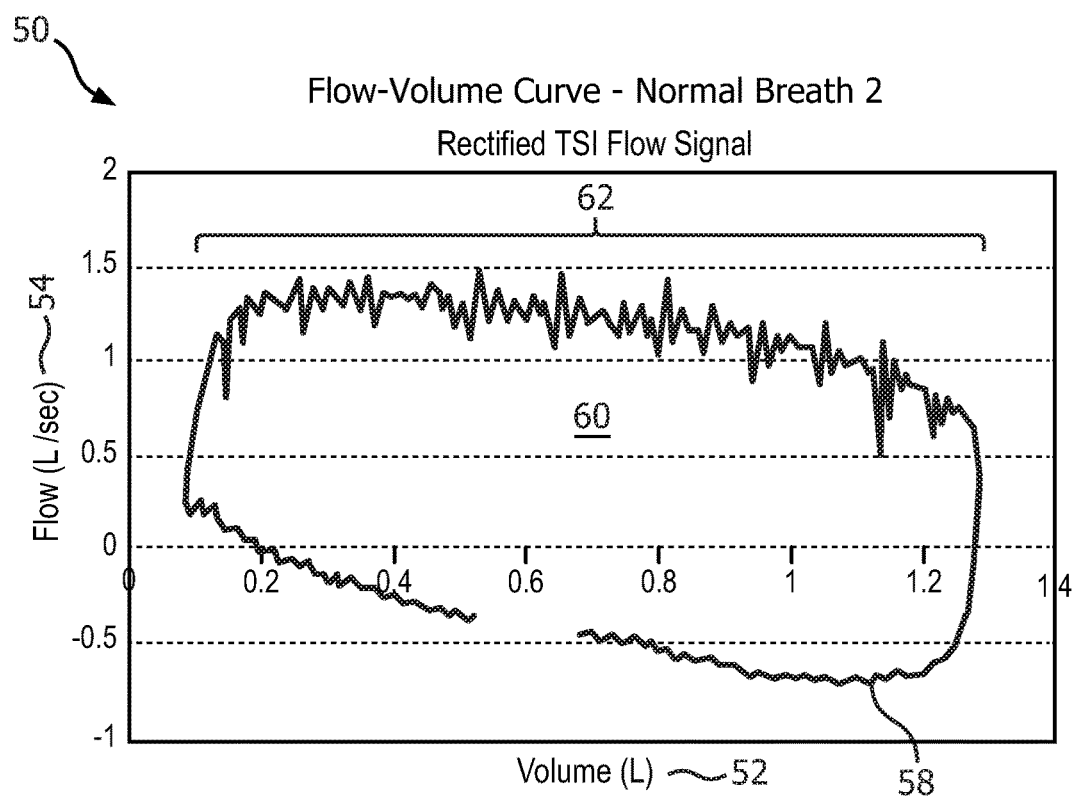
FIG. 3 is a plot of flow rate versus volume during at least one inspiration and expiration of a subject with a noisy signal indicating a need to effectuate initiation of airway clearance for the subject.

FIGS. 2 and 3 illustrate how secretion determination component 34 may compare a non-noisy signal 56 (as illustrated in FIG. 2) with a noisy signal 62 (illustrated in FIG. 3) of the same subject 12. During inhalation, subject 12 without secretions obstructing the airway will generate a relatively smooth inspiratory signal 56 as plotted by parameter component 30 and illustrated in FIG. 2. Such a signal may be used by analysis component 32 (FIG. 1) to determine a baseline and/or threshold value for Φ, for example. When an obstruction occludes an airway of subject 12 the signal becomes more ragged generating a noisy inspiratory signal 62, as illustrated in FIG. 3. Analysis component 32 (FIG. 1) determines the perimeter 58, area 60, and/or other parameters of the plots shown in FIG. 2 and/or FIG. 3 and determines Φ in both cases (e.g., previous respiration shown in FIG. 2 and a current respiratory cycle as shown in FIG. 3) for comparison. In this way, analysis component 32 can determine in real time the dimensionless quantity Φ which amplifies the noise of the signal (e.g., because the perimeter 58 is squared) and normalizes the signal by the area 60 of normal inspiration and expiration cycles by subject 12 (e.g., the area 60 of the geometric shaped formed by the plot 50 of flow rate versus volume). In this way secretion determination component 34 (FIG. 1) can compare Φ for a current breathing cycle from analysis component 32 to the threshold and/or baseline Φ determined for subject 12 based on previous respiration to determine whether to effectuate initiation of airway clearance for subject 12.

Secretion determination component 34 may be configured to effectuate airway clearance for subject 12 responsive to Φ for a current breathing cycle breaching the threshold and/or baseline value for Φ. Secretion detection component 34 may be configured to effectuate airway clearance responsive to a single breach of the threshold value, one or more breaches of the threshold value, an average value for Φ breaching the threshold value and/or other breaches of the threshold value. Secretion determination component 34 may effectuate airway clearance for subject 12 by controlling pressure generator 14 (FIG. 1) to switch from a pressure support therapy and/or ventilation therapy mode (e.g., controlled by control component 36 described below) to operate in an airway clearance therapy mode. Once airway clearance is complete, secretion determination component 34 may be configured to cause pressure generator 14 to return to the pressure support therapy and/or ventilation therapy mode (e.g., control component 36 may resume control over pressure generator 14).

Control component 36 is configured to control pressure generator 14 to provide respiratory therapy to subject 12. Control component 36 is configured to control pressure generator 14 based on the output signals from sensors 18, parameters determined by parameter component 30, information entered and/or selected via user interface 22, and/or other information. In some embodiments, control component 36 is configured such that controlling pressure generator 14 to provide respiratory therapy to subject 12 includes controlling pressure generator 14 to provide the pressurized flow of breathable gas to the airway of subject 12 according to a positive airway pressure support therapy regime (e.g., CPAP, APAP, BiPAP), according to a ventilation therapy regime, and/or according to other respiratory therapy regimes. In some embodiments, control component 36 is configured to control pressure generator 14 to provide a minimum amount of positive airway pressure support during inhalation (e.g., IPAP) and/or exhalation (e.g., EPAP).

Figures 4, 5:
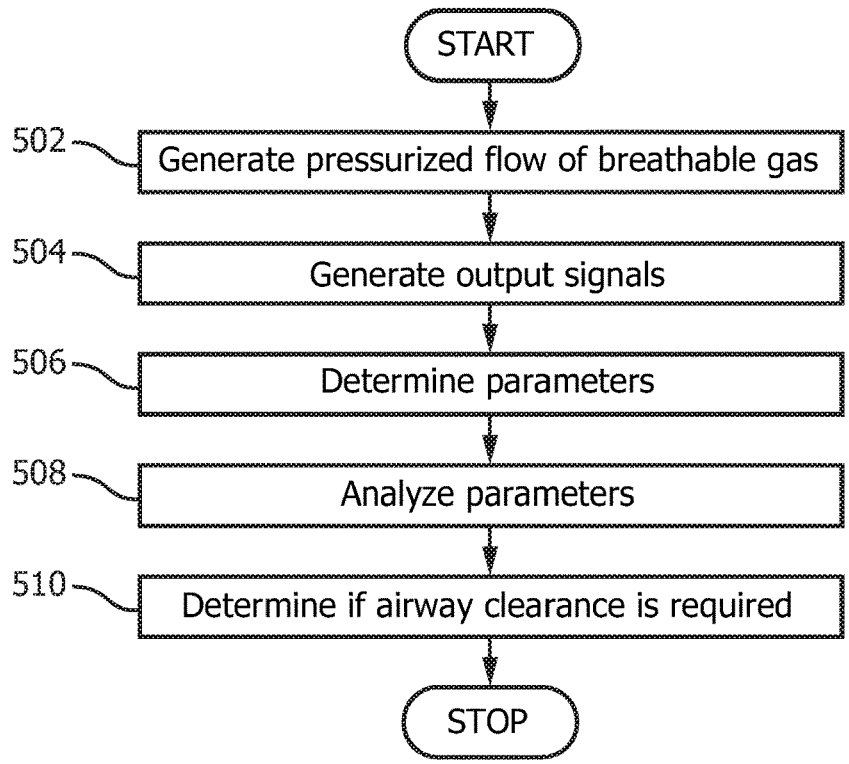
FIG. 4 is a table illustrating the dimensionless qualities of the perimeter squared normalized by the area of a variety of shapes.
FIG. 5 illustrates a method to determine whether the subject requires airway clearance.

FIG. 4 illustrates how the dimensionless number Φ retains a constant numeric quantity for a given shape regardless of the size of the shape. For example, a square will have a calculated Φ of 16 regardless of the size of the square. Similarly, a circle will have a determined value of 12.6 for Φ regardless of the radius of the circle. Rectangles can be categorized by the ratio of the height (h) to the base (n*h). This property of Φ is useful because the expected value of a shape enables an estimation of the threshold for secretion determination component 34. For example, if the shape of subjects 12 plot is a square the threshold value set by secretion determination component 34 could be predetermined (e.g., at manufacture, based on entries and/or selections via user interface 22, etc.) to be 16. In some embodiments a small deviation from the predicted value may be tolerated (e.g., by setting the threshold value at a number greater than 16). In this example, a care-giver and/or secretion determination component 34 could determine that any value of Φ less than 20 is acceptable, for example. This provides a threshold to compare the real time values of Φ determined by analysis component 32.

Returning to FIG. 1 user interface 22 is configured to provide an interface between system 10 and subject 12, and/or other users through which subject 12 and/or other users may provide information to and receive information from system 10. Other users may comprise, for example, a caregiver, a doctor, and/or other users. This enables data, cues, results, and/or instructions and any other communicable items, collectively referred to as "information," to be communicated between a user (e.g., subject 12) and one or more of pressure generator 14, processor 20, and/or other components of system 10. For example, therapy pressures, the breath rate of subject 12, a plot of flow rate versus volume, and/or other information may be displayed to a user (e.g., subject 12) via user interface 22.

Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, wireless communications to a secondary device (e.g. a phone, tablet, iPad, and/or secondary devices), and/or other interface devices. In some embodiments, user interface 22 comprises a plurality of separate interfaces.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, etc.).

Control module 58 is configured to control pressure generator 14 to generate the pulse of breathable gas for delivery to the airway of subject 12. Control module 58 is configured to control pressure generator 14 to deliver the pulse responsive to detection of respiratory sleep events (e.g., airway obstruction) by respiratory event detection module 54. The pulse is delivered to the airway of subject 12 such that the airway of subject 12 is opened prior to a subsequent inhalation and/or ventilation. Control module 58 is configured to control pressure generator 14 to deliver the pulse in accordance with the pulse parameters obtained and/or adjusted by pulse parameter module 56 prior to the pulse. For example, control module 58 may be configured to control pressure generator 14 to deliver the pulse responsive to detection of airway obstruction and/or in accordance with a timing obtained by pulse parameter module 56. In some embodiments, the pulse of breathable gas can be a square wave. Moreover, the square wave can have smooth edges to increase comfort and decrease the likelihood of arousing subject 12. In some embodiments, the pulse of breathable gas can be a saw wave with a ramping time adjusted based on efficacy of the therapy to mitigate obstructions during respiration. Finally, the parameters that will control the duration and magnitude of the pulse of breathable gas may initially be selected from a control menu and then automatically adjusted by control module 58 based on the statistical effectiveness in clearing the airway obstruction of the previous pulses.

Control module 58 is configured to control pressure generator 14 to provide the pressurized flow of breathable gas to the airway of the subject according to a positive airway pressure support therapy regime (e.g., CPAP, APAP, BiPAP). Control module 58 is configured to control pressure generator 14 to provide a minimum amount of positive airway pressure support during inhalation (e.g., IPAP) and/or exhalation (e.g., EPAP). Delivering a minimum amount of pressure support and providing a pulse when needed may increase the comfort level of subject 12 during therapy. The minimum amount of positive airway pressure support may comprise delivering the pressurized flow of breathable gas at a minimum pressure level. The minimum pressure level may be configured such that carbon dioxide re-breathing is substantially avoided during pressure support therapy. In some embodiments, the inhalation positive airway pressure may be less than about 7 $cmH_2O$. In some embodiments, the inhalation positive airway pressure may be between about 1 $cmH_2O$ and about 7 $cmH_2O$. In some embodiments, the inhalation positive airway pressure level may be zero if there is no carbon dioxide rebreathing by subject 12. Control module 58 controls pressure generator 14 to deliver the pulse as needed in addition to the positive airway pressure support.

Control module 58 is configured to control pressure generator 14 to generate pulses as needed such that subject 12 may maintain a regular breathing pattern. FIG. 5 illustrates a regular flow rate profile 500 for four consecutive breaths 502, 504, 506, and 508. One or more of breaths 502, 504, 506, and/or 508 may be preceded by the control module (shown in FIG. 1) controlling the pressure generator (shown in FIG. 1) to generate a pulse for delivery to the airway of the subject (shown in FIG. 1) such that the subject's airway is opened prior to and/or at the beginning of the inhalation.

Information determined by processor 20 and/or stored by electronic storage 24 may comprise information related to a threshold value of Φ, a current value of Φ, and/or other information. The information stored by electronic storage 24 may be viewed via user interface 22, by connecting (wired and/or wireless) to a separate computer, and/or other via other methods. The information stored by electronic storage 24 may be used, for example, by a doctor to make medical decisions, and/or for other uses. In some embodiments, system 10 may include a wireless transmitter (not shown) and the information determined by processor 20, the information stored by electronic storage 24, and/or other information may be communicated to a care giver, for example, over a wireless network. By way of a non-limiting example, the care giver may receive use information, patient status, and/or other information, allowing the care giver to remotely track the therapy delivered by system 10.

FIG. 5 illustrates a method 500 of delivering a pressurized flow of breathable gas to the airway of a subject and to detect a presence of secretions in an airway of a subject 12 during respiratory therapy to determine whether the subject requires airway clearance. System 10 contains a pressure generator, a subject interface, one or more sensors, and one or more processors. The one or more processors are configured to execute computer program components. The computer program components include a parameter component, an analysis component, a secretion determination component, and/or other components. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, a pressurized flow of breathable gas for delivery to the airway of the subject is generated with the pressure generator. In some embodiments, operation 502 is performed by a pressure generator the same as or similar to pressure generator 14 (shown in FIG. 1 and described herein).

At an operation 504, one or more output signals conveying information related to one or more gas parameters of the pressurized flow of breathable gas delivered to the airway of the subject are generated with the one or more sensors. In some embodiments, operation 504 is performed by sensors the same as or similar to sensors 18 (shown in FIG. 1 and described herein).

At an operation 508, a first gas parameter that indicates a volume of breathable gas within the airway of the subject and a second gas parameter that is a time derivative of the first gas parameter are determined. In some embodiments, operation 508 is performed by a parameter component is the same as or similar to parameter component 30 (shown in FIG. 1 and described herein).

At an operation 510, a determination of whether to effectuate initiation of airway clearance for the subject based on a perimeter of a plot of the first gas parameter versus the second gas parameter for a complete breathing cycle that includes an inhalation and an exhalation. Secretions are identified based on the noise level in the output signals and/or the determined parameters. In some embodiments, operation 510 is performed by a secretion determination component 34 the same as or similar to secretion determination component 34 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to detect a presence of secretions in an airway of a subject during respiratory therapy and determine that the subject requires airway clearance, the system comprising:

a pressure generator configured to generate a pressurized flow of breathable gas for delivery to the airway of the subject;

one or more sensors configured to generate output signals that convey information related to one or more gas parameters of the pressurized flow of the breathable gas delivered to the airway of the subject; and one or more physical computer processors operatively connected to the pressure generator and the one or more sensors, the one or more physical computer processors configured by computer readable instructions to:

determine a first gas parameter that indicates a volume of the breathable gas within the airway of the subject;

determine a second gas parameter that is a time derivative of the first gas parameter;

determine a perimeter of a plot of the first gas parameter versus the second gas parameter for a complete breathing cycle that includes both an inhalation and an exhalation;

determine an area of the plot;

square the perimeter of the plot by multiplying the perimeter by itself;

normalize the square of the perimeter of the plot by the area of the plot to produce a clearance metric configured to amplify a noise signal of the perimeter, wherein the one or more physical computer processors are configured such that the second gas parameter is a flow rate of breathable gas inhaled and exhaled by the subject during the complete breathing cycle, and the first gas parameter is the volume of breathable gas within the airway of the subject for the complete breathing cycle;

compare a current value of the clearance metric to a threshold value of the clearance metric; and initiate the airway clearance of the subject based upon the comparison.

2. The system of claim 1, wherein the one or more physical computer processors are further configured by computer readable instructions to initiate the airway clearance after a single breach of the threshold value of the clearance metric.

3. The system of claim 1, wherein the one or more physical computer processors are further configured by computer readable instructions to initiate the airway clearance after a plurality of breaches of the threshold value of the clearance metric.

4. The system of claim 1, wherein the one or more physical computer processors are further configured by computer readable instructions to initiate the airway clearance after an average value of the clearance metric breaches the threshold value of the clearance metric.

5. A method of operation of a detection system, the detection system comprising a pressure generator, one or more sensors, and one or more physical computer processors, the method comprising:

generating, with the pressure generator, a pressurized flow of breathable gas;

generating, with the one or more sensors, output signals that convey information related to one or more gas parameters of the pressurized flow of the breathable gas;

determining, with the one or more physical computer processors, a first gas parameter that indicates a volume of the breathable gas;

determining, with the one or more physical computer processors, a second gas parameter that is a time derivative of the first gas parameter;

determining, with the one or more physical computer processors, a perimeter of a plot of the first gas parameter versus the second gas parameter for a complete breathing cycle that includes both an inhalation and an exhalation;

determining, with the one or more physical computer processors, an area of the plot;

squaring, with the one or more physical computer processors, the perimeter of the plot by multiplying the perimeter by itself;

normalizing, with the one or more physical computer processors, the square of the perimeter of the plot by the area of the plot to produce a clearance metric configured to amplify a noise signal of the perimeter, wherein the one or more physical computer processors are configured such that the second gas parameter is a flow rate of the breathable gas inhaled and exhaled during the complete breathing cycle, and the first gas parameter is the volume of the breathable gas for the complete breathing cycle;

comparing a current value of the clearance metric to a threshold value of the clearance metric; and initiating the airway clearance of the subject based upon the comparison.

6. The method of claim 5, further comprising:
initiating the airway clearance after a single breach of the threshold value of the clearance metric.

7. The method of claim 5, further comprising:
initiating the airway clearance after a plurality of breaches of the threshold value of the clearance metric.

8. The method of claim 5, further comprising:
initiating the airway clearance after an average value of the clearance metric breaches the threshold value of the clearance metric.

* * * * *